United States Patent [19]

Frazier et al.

[11] Patent Number: 4,741,768

[45] Date of Patent: May 3, 1988

[54] HERBICIDAL SUBSTITUTED 2-[1-(3-TRANS-CHLORO-ALLYLOXYAMINO)ALKYLIDENE]-CYCLOHEXANE DIONE SALTS

[75] Inventors: Rawls H. Frazier, Petaluma; Tatao Luo, El Sobrante, both of Calif.

[73] Assignee: Chevron Research Company, San Francisco, Calif.

[21] Appl. No.: 876,330

[22] Filed: Jun. 19, 1986

Related U.S. Application Data

[63] Continuation-in-part of Ser. No. 657,697, Oct. 9, 1984, abandoned, and Ser. No. 798,670, Nov. 15, 1985, abandoned.

[51] Int. Cl.[4] ............................................. C07C 131/00
[52] U.S. Cl. ........................................... 71/98; 556/37; 564/256
[58] Field of Search .................. 556/37; 564/256; 71/98

[56] References Cited

U.S. PATENT DOCUMENTS

| | | | |
|---|---|---|---|
| 4,249,937 | 2/1981 | Iwataki et al. | 556/37 X |
| 4,440,566 | 4/1984 | Luo | 71/98 |
| 4,482,740 | 11/1984 | Iwataki et al. | 556/37 X |
| 4,504,305 | 3/1985 | Iwataki et al. | 71/98 |
| 4,515,729 | 5/1985 | Iwataki et al. | 71/98 X |
| 4,517,013 | 5/1985 | Becker et al. | 71/98 |
| 4,555,263 | 11/1985 | Serban et al. | 71/98 |
| 4,617,050 | 10/1986 | Jahn et al. | 71/98 |
| 4,626,276 | 12/1986 | Luo | 564/256 X |

FOREIGN PATENT DOCUMENTS

| | | | |
|---|---|---|---|
| 0082694 | 6/1983 | European Pat. Off. | 564/256 |
| 59-155353 | 9/1984 | Japan | 564/256 |
| 2090246 | 7/1982 | United Kingdom | 564/256 |

*Primary Examiner*—Paul F. Shaver
*Attorney, Agent, or Firm*—S. R. La Paglia; T. G. DeJonghe; L. S. Squires

[57] ABSTRACT

Cupric, lithium, and magnesium salts of trans-substituted 2-[1-(3-chloroallyloxyimino)alkylidene]-cyclohexane-1,3-dione and derivatives thereof. The compounds generally exhibit improved stability and enhanced shelf-life while retaining excellent pre-emergence and post-emergence grassy weed phytotoxicity. The compounds are useful as selective herbicides and at low dosages as plant growth regulating agents.

27 Claims, No Drawings

HERBICIDAL SUBSTITUTED 2-[1-(3-TRANS-CHLORO-ALLYLOXYAMINO)ALKYLIDENE]-CYCLOHEXANE DIONE SALTS

CROSS-REFERENCE TO RELATED APPLICATIONS

This application is a continuation-in-part of copending U.S. application Ser. No. 657,697, filed Oct. 9, 1984 now abandoned and U.S. Ser. No. 798,670, filed Nov. 15, 1985 and now abandoned.

BACKGROUND OF THE INVENTION

This invention relates to copper, magnesium and lithium salts of certain substituted 2-[1-(oxyamino)alkylidene]cyclohexane diones and to the use of such compounds as herbicides and plant growth regulators.

U.S. Pat. No. 4,440,556 generically discloses cation salts of 2-[1-(3-trans-chloroallyloxyimino)-alkyl]-5-(alkyl, alkylthio and alkylthioalkyl)cyclohexane-1,3-diones and specifically lists sodium, ammonia, calcium, etc. as examples of such salts.

A number of 2-substituted iminoalkyl 5-substituted cyclohexane 1,3-diones and cation salts thereof are described in U.S. Pat. Nos. 3,943,176; 3,989,737; 3,950,420; 4,011,256; 4,033,754; 4,249,937; published European Patent Application No. 46860 and published German Patent Application Nos. DE 3,219,315; DE 3,227,389; DE 3,227,332. For example, various illustrative cations listed in these references include sodium, potassium, calcium, barium, manganese, copper, zinc, nickel, cobalt, iron, silver (see U.S. Pat. No. 4,011,256—column 4, U.S. Pat. No. 4,249,937—column 2) and alkali metal sodium, potassium, manganese, copper, zinc, iron, barium (see U.S. Pat. No. 4,422,864—column 3).

2-[1-(3-trans-chloroallyloxyimino)alkyl]-5-(alkylthioalkyl)cyclohexane-1,3-diones, such as described in U.S. Pat. No. 4,440,556 and in commonly-assigned copending application Ser. No. 798,670, filed Nov. 15, 1984 are excellent selective grass herbicides. However, it would be desirable to improve the storage stability of these compounds, both with respect to temperature and high humidity or moisture.

SUMMARY OF THE INVENTION

The present invention provides compounds having both pre-emergence and post-emergence grassy weed herbicidal activity and having good safety in a number of broadleaf crops. Moreover, these compounds exhibit improved storage stability. At lower application rates the compounds can be used as plant growth regulators. The salts of the present invention have improved stabilities and shelf lives while retaining the excellent herbicidal properties of the parent compounds.

The compounds of the present invention can be represented by the following formula:

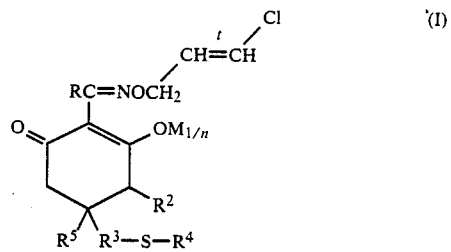

wherein M is a cation selected from the group of copper (i.e., cupric), magnesium, and lithium and n is its valence;

R is lower alkyl having 1 through 4 carbon atoms;

$R^2$ is hydrogen, or alkoxycarbonyl having 2 through 6 carbon atoms;

$R^3$ is lower alkylene having 1 through 6 carbon atoms and includes both straight chain and branched chain alkylene groups;

$R^4$ is lower alkyl having 1 through 6 carbon atoms phenyl or substituted phenyl having 1 through 3 substituents independently selected from the group of lower alkyl having 1 through 6 carbon atoms, lower alkoxy having 1 through 6 carbon atoms, halo, and haloalkyl having 1 through 4 carbon atoms and 1 through 3 of the same or different halo atoms; and $R^5$ is hydrogen or lower alkyl; and the double bond designation $\pm$ indicates the compound is trans geometrically oriented with respect to the double bond.

The compounds of Formula (I) also have an asymmetric carbon atom and can also exist as optical isomers. As above noted the compounds of Formula I are trans geometric isomers with respect to the 3-chloroallyl double bond. Additional ion bonding can also occur between cation M and the nitrogen groups. In some instances the compounds also exist as further geometric isomers with respect to other groups. The above formula is intended to encompass the respective individual isomers as well as mixtures thereof and the respective isomers as well as mixtures thereof are encompassed within the invention.

In a further aspect the invention provides a herbicidal composition comprising a compatible carrier and a herbicidally effective amount of the compound(s) of the invention or mixtures thereof.

The present invention also provides a method for preventing or controlling the growth of unwanted vegetation, which comprises treating the growth medium and/or the foliage of such vegetation with a herbicidally effective amount of the compound(s) of the invention or mixtures thereof.

In another aspect, the present invention provides a plant growth regulating composition comprising a compatible carrier and a plant growth regulating amount of the compound(s) the invention or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of the invention or mixtures thereof, effective to alter the normal growth pattern of said plants.

The present invention also provides processes for preparing the compounds of the invention.

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 1–4 set forth hereinbelow on Pages 11–16. In terms of substituents, the preferred compounds are those wherein R is methyl, ethyl, or propyl and especially ethyl and propyl; $R^2$ is preferably hydrogen; $R^3$ is preferably branched alkylene having 2 through 4 carbon atoms; and more preferably is $-CH_2CH(CH_3)-$; $R^4$ is preferably alkyl having 1 through 4 carbon atoms, $R^5$ is preferably lower alkyl having 1 through 4 carbon atoms and more preferably is hydrogen. Most preferably, $-R^3-S-R^4$ is $-CH_2CH(CH_3)SCH_2CH_3$ or $-CH_2CH(CH_3)SCH_3$ and $R^5$ is hydrogen. Preferably, M is cupric or magnesium.

The preferred compounds have at least one preferred substituent and most preferably, the compounds contain a combination of two or more preferred substituents.

The compounds of Formula (I) can be conveniently prepared via treatment of the corresponding appropriately substituted 3-hydroxy cyclohex-2-en-1-one or the 3-sodium or 3-potassium salts thereof with the desired M base. In the case where M is copper++ or magnesium, the compounds can also be prepared via the reaction of the corresponding 1,3-dione with the desired M base. These reactions can be schematically represented by the overall reaction equation:

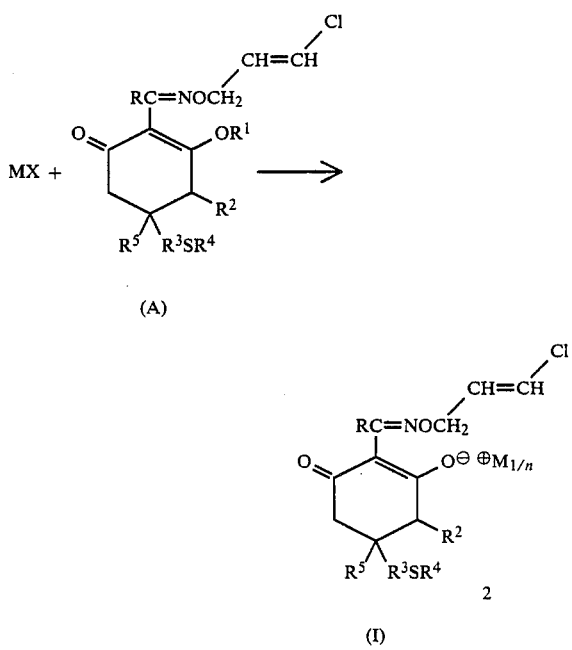

wherein $R^1$ is hydrogen sodium or potassium, MX is a salt or base and R, $R^2$, $R^3$, $R^4$, $R^5$, M and n are as defined hereinabove.

This process can be conveniently effected by contacting Compound (A) wherein $R^1$ is sodium or potassium, under reactive conditions with an acidic cupric or magnesium salt (MX) having the desired M cation or by reacting the compound of formula A, wherein $R^1$ is hydrogen with the appropriate M base. Preferably, these reactions are conducted an inert solvent.

Typically, these processes are conducted at temperatures in the range of about from 5° to 30° C., preferably about from 20° to 25° C., for about from 1 to 16 hours, preferably about from 2 to 8 hours, preferably using stoichiometric amounts of reactants or an excess of the M salt or the M base. Suitable inert solvents which can be used include, for example, water, tetrahydrofuran and the like. Generally, where an MX salt is used, it is preferred to use a water soluble MX salt and conduct the reaction in water, since typically starting material (A) is also water soluble.

Suitable salts which can be used include, for example, sulfates, chlorides, acetates and the like. Suitable bases include copper dialkoxides, magnesium dialkoxides, lithium hydroxide, lithium alkoxides and the like.

The starting materials of Formula (A) can be prepared via the procedures described in U.S. Pat. No. 4,440,556. The sodium and potassium salts (A) can be prepared, for example, by reacting the corresponding free acid (i.e., Formula A if $R^1$ is H) with a sodium base (e.g., NaOH) or potassium base (e.g., KOH).

General Process Conditions

In the above-described process, the products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkylene" refers to both straight chained and branched chained alkylene groups having 1 through 6 carbon atoms, preferably 1 through 4 carbon atoms and includes, for example,

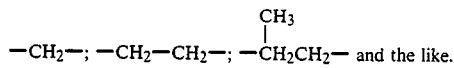

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"—wherein R' and R" are independently straight chain or branched chain alkyl groups having 1 through 3 carbon atoms.

The term "lower alkylthioalkyl" refers to the group R'SR"—wherein R' and R" are independently straight chain or branched chain alkyl groups having 1 through 3 carbon atoms.

The term "lower alkoxycarbonylalkyl" refers to the group

wherein R' is lower alkyl, preferably having 1 through 4 carbon atoms, and R" is alkylene having 1 through 4 carbon atoms and can be straight or branched chained. Typical alkoxycarbonylalkyl groups include for example, —CH$_2$C(O)OCH$_3$; —CH(CH$_3$)C(O)OC$_2$H$_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms. The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "room temperature" or "ambient temperature" refers to about 20°-25° C.

Utility

The compounds of Formula (I) exhibit excellent pre-emergence and post-emergence grassy weed herbicidal activity and also exhibit very good soil stability. Moreover, as well as exhibiting these desirable herbicidal properties, the compounds also exhibit substantially improved storage stability and improved shelf-life.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of the plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds. At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

Example 1

Lithium 2-1-[3-chloro-trans-allyloxyimino)butyl]-5-(2-ethylthiopropyl)cyclohex-2-en-1-one-3-olate

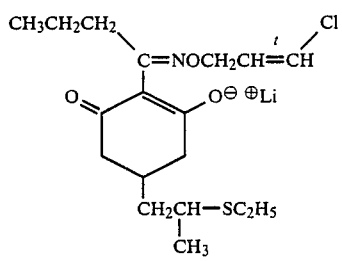

In this example, 15.9 g of 2-[1-(3-transchloroallyloxyimino)butyl]-3-hydroxy-5-(2-ethylthiopropyl)cyclohex-2-en-1-one was stirred into 180 ml of hexane under a nitrogen atmosphere and surrounded by a dry ice/acetone bath. The mixture was stirred until at least the major portion of the 2-[1-(3-trans-chloroallyloxyimino)butyl]-3-hydroxy-5-(2-ethylthiopropyl)-cyclohex-2-en-1-one had dissolved and then 26.6 ml (1.6 g-moles) of t-butyllithium was added. The addition was interrupted to add additional hexane to maintain reaction mixture as a slurry. The mixture was stirred overnight (about 16–18 hours) and then filtered. The filter cake was washed with hexane and then dried in a vacuum oven, affording the title compound.

Similarly, by applying the above procedure using the corresponding starting materials the following lithium salts can be prepared:
lithium 2-[1-(3-trans-chloroallyloxyimino)butyl]-4-ethoxycarbonyl-5-(2-ethylthiopropyl)-cyclohex-2-en-1-one-3-olate;
lithium 2-[1-(3-trans-chloroallyloxyimino)hexyl]-5-(2-ethylthiopropyl)-cyclohex-2-en-1-one-3-olate;
lithium 2-[1-(3-chloro-trans-allyloxyimino)ethyl]-4-methoxycarbonyl-5-(2-ethylthiopropyl)-cyclohex-2-en-1-one)-3-olate;
lithium 2-[1-(3-trans-chloroallyloxyimino)pentyl]-5-(2-ethylthiopropyl)-cyclohex-2-en-1-one-3-olate;
lithium 2-[1-(3-trans-chloroallyloxyimino)butyl]-5-(2-isopropylthiopropyl)-cyclohex-2-en-1-one-3-olate;
lithium 2-[1-(3-trans-chloroallyloxyimino)propyl]-5-(2-ethylthiopropyl)-cyclohex-2-en-1-one-3-olate;
lithium 2-[1-(3-trans-chloroallyloxyimino)propyl]-5-(2-propylthiopropyl)-cyclohex-2-en-1-one-3-olate.

Example 2

3-Magnesium Salt of bis(-2-[1-(3-chloro-transallyloxy-imino)butyl]-3-hydroxy-5-(2-ethylthiopropyl)-cyclohex-2-en-1-one)

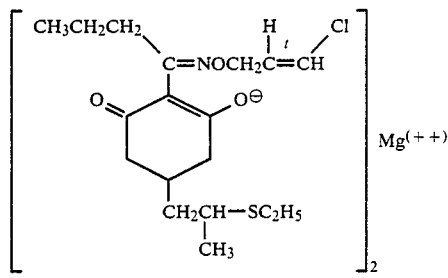

In this example 0.16 g of magnesium turnings in 25 ml of anhydrous methanol was refluxed under nitrogen for three hours, resulting in the formation of magnesium dimethoxide. The reaction mixture was vacuum evaporated to remove methanol and then slurried with 10 ml of tetrahydrofuran under nitrogen. A solution containing 5 g of 2-[1-(3-trans-chloroallyloxyimino)butyl]-3-hydroxy-5-(2-ethylthiopropyl)-cyclohex-2-en-1-one in 5 ml of anhydrous tetrahydrofuran was admixed thereto at room temperature. The resulting mixture was stirred overnight, about 16 hours, at room temperature under nitrogen. The mixture was then mixed with a small amount of tetrahydrofuran and stirred for an additional three hours and then evaporated to remove the tetrahydrofuran. The residue was slurried in 50 ml of hexane and filtered. The filter cake was washed twice with hexane and then evaporated under dryness affording the title compound.

Similarly, by applying the above procedure using the corresponding 3-hydroxy starting materials the following magnesium salts can be prepared:
magnesium bis(2-[1-(3-trans-chloroallyloxyimino)-butyl]-4-isopropoxycarbonyl-5-(2-ethylthiopropyl)-cyclohex-2-en-1-one-3-olate);
magnesium bis(2-[1-(3-chloro-trans-allyloxyimino)-propyl]-5-(3-ethylthiopropyl)-cyclohex-2-en-1-one-3-olate);
magnesium bis(2-[1-(3-chloro-trans-allyloxyimino)ethyl]-5-(2-ethylthiopropyl)-cyclohex-2-en-1-one-3-olate);
magnesium bis(2-[3-methyl-1-(3-trans-chloroallyloxyimino)-butyl]-5-(2-ethylthiopropyl)-cyclohex-2-en-1-one-3-olate);
magnesium bis(2-[1-(3-trans-chloroallyloxyimino)-butyl]-5-(3-hexylthiohexyl)-cyclohex-2-en-1-one-3-olate);
magnesium bis(2-[1-(3-trans-chloroallyloxyimino)-propyl]-5-(2-ethylthiopropyl)-cyclohex-2-en-1-one-3-olate;
magnesium bis(2-[1-(3-trans-chloroallyloxyimino)-propyl]-5-2-methylthiopropyl)-cyclohex-2-en-1-one-3-olate; and magnesium bis(2-[1-(3-trans-chloroallyloxyimino)-propyl]-5-(2-propylthioethyl)-cyclohex-2-en-1-one-3-olate.

EXAMPLE 3

3-Cupric Salt of 2-[1-(3trans-chloroallyloxyimino)butyl]-5-(2-ethylthiopropyl)cyclohex-2-en-1-one-3-olate $$\left[\begin{array}{c} CH_3CH_2CH_2 \diagdown \phantom{xx} \diagup Cl \\ C=NOCH_2CH=CH \\ O= \phantom{xxx} O^\ominus \\ \phantom{xxxx} \\ CH_2CH-SC_2H_5 \\ | \\ CH_3 \end{array}\right]_2 Cu^{(++)}$$

In this example, 1.25 g of cupric sulfate hydrate (CuSO$_4$.5H$_2$O) was dissolved in 5 ml of water and added dropwise to 5 ml of an aqueous solution of containing 3.73 g of the sodium salt of 2-[1-(3-transchloroallyloxyimino)butyl]-3-hydroxy-5-(2-ethylthiopropyl)-cyclohex-2-en-1-one at room temperature. (The sodium salt was previously prepared via the reaction of the 1,3-dione with aqueous sodium hydroxide.) The mixture was stirred overnight (about 16 hours) at room temperature and then 10 ml of methylene chloride was mixed in. The mixture was stirred for another 3 hours at room temperature and filtered. The methylene chloride layer of the filtrate was separated from the water layer and evaporated to dryness affording the title compound as a solid residue.

Elemental analysis carbon: calc. 53.4 wt.%, found 52.6 wt. %; hydrogen: calc. 6.72 wt.%, found 6.78 wt. %; nitrogen: calc. 3.45 wt. %, found 3.48 wt. %.

Similarly, by applying the above procedure using the corresponding sodium salts as starting materials the of the following cupric salts can be prepared:
copper bis(2-[(1-(3-trans-chloroallyloxyimino)butyl]-4-methoxycarbonyl-5-(2-ethylthiopropyl)-cyclohexen-1-one-3-olate);
copper bis(2-[1-(3-trans-chloroallyloxyimino)propyl]-5-(2-ethylthiopropyl)-cyclohexen-1-one-3-olate);
copper bis(2-[1-(3-trans-chloroallyloxyimino)ethyl]-5-(2-ethylthiopropyl)-cyclohexen-1-one-3-olate);
copper bis(2-[2-methyl-1-(3-trans-chloroallyloxyimino)-butyl]-5-(2-ethylthiopropyl)cyclohexen-1-one-3-olate);
copper bis(2-[1-(3-trans-chloroallyloxyimino)butyl]-5-(3-t-butylthiopentyl)-cyclohexen-1-one-3-olate);
copper bis(2-[1-(3-trans-chloroallyloxyimino)propyl]-5-(2-ethylthiopropyl)-cyclohex-2-en-1-one-3-olate);
copper bis(2-[1-(3-trans-chloroallyloxyimino)propyl]-5-2-methylthiopropyl)-cyclohex-2-en-1-one-3-olate); and
copper bis(2-[1-(3-trans-chloroallyloxyimino)propyl]-5-(2-propylthioethyl)-cyclohex-2-en-1-one-3-olate).

The title compounds of Examples 1-3 are listed in Table A hereinbelow.

TABLE A $$\begin{array}{c} \phantom{xxxx} Cl \\ RC=NOCH_2CH=CH \\ O= \phantom{xxx} O^{(-)}M_{1/n} \\ \phantom{xxxx} \\ H \phantom{xx} CH_2CHSCH_2CH_3 \\ \phantom{xxxxxxxx} | \\ \phantom{xxxxxxxx} CH_3 \end{array}$$

| No. | M | n | R | Melting Point °C. |
|---|---|---|---|---|
| 1 | Li$^+$ | 1 | (CH$_2$)$_2$CH$_3$ | —* |
| 2 | Mg$^{++}$ | 2 | (CH$_2$)$_2$CH$_3$ | 170** |
| 3 | Cu$^{++}$ | 2 | (CH$_2$)$_2$CH$_3$ | 112–115 |

*= Highly hydroscopic
**= Decomposition

EXAMPLE 4

In this example, the compounds of Table A above, and were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 27.5 micrograms/cm$^2$ unless otherwise specified in the following Tables. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$ unless otherwise specified in the following Tables. After the plants had dried, they were placed in a greenhouse and then watered intermittently at their base as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm$^2$,
unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mustard | Pigweed | Soybean | Watergrass | Crabgrass | Wild Oats | Rice |
| 1* | — | — | — | — | 100 | 99 | 92 | 100 |
| 2 | 0 | 0 | 0 | 0 | 100 | 100 | 100 | 100 |
| 3 | 0 | 10 | 0 | 15 | 100 | 100 | 100 | 100 |

*Tested at 1.8 microgram/cm$^2$

TABLE 2

Post-Emergence Herbicidal Activity
Application Rate: 27.5 micrograms/cm$^2$,
unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mustard | Pigweed | Soybean | Watergrass | Crabgrass | Wild Oats | Rice |
| 1* | — | — | — | — | 100 | 91 | 91 | 98 |
| 2 | 0 | 0 | 0 | 0 | 100 | 100 | 100 | 100 |
| 3 | 0 | 0 | 0 | 0 | 100 | 100 | 100 | 100 |

*Tested at 1.8 microgram/cm$^2$

As can be seen from the above Tables, the compounds of the invention of excellent selective herbicides and exhibit excellent pre-emergence and post-emergence phytotoxicity against grasses yet are safe with respect to broad-leaf plants.

EXAMPLE 5

In this example stability tests were conducted on a variety of salts and the free acid (R=H). These tests were conducted using about from 2 to 5 g samples of the material as received from the synthesis laboratory. Upon receipt, the material was analyzed to determine the amount (percent) of active material. The remaining material in the sample was primarily left over salt or base used as starting material in the synthesis of the salt. The assays were determined by analyzing for the free acid (R=H) and then adjusting to the particular salt on the bases of molecular weights.

About 2 to 5 g of the material was sealed in a glass vial and then placed in an oven set at 50° C. (in some instances a second sample was also run at room temperature.) After about 2 to 2½ months the samples were examined and reanalyzed and the percent retention of active material determined, i.e., (percent material finish ÷ percent material start) × 100 = percent retention.

Where stability problems were noted, the samples were examined at earlier times.

The compounds tested and results of this testing are summarized in Table 3 hereinbelow.

TABLE 3

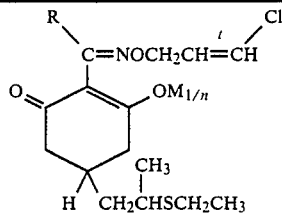

| Compound No. | R | M | n | Temperature °C. | Months on Test | Percent Active Material | | % Retention of Active Material |
|---|---|---|---|---|---|---|---|---|
| | | | | | | Start | Finish | |
| 1 | CH$_3$CH$_2$CH$_2$— | Li | 1 | RT* | 2.4 | 69.3 | 64.5 | 93.1 |
| 1 | CH$_3$CH$_2$CH$_2$— | Li | 1 | 50 | 2.4 | 69.3 | 56.4 | 81.4 |
| 2 | CH$_3$CH$_2$CH$_2$— | Cu | 2 | RT | 2.3 | 78.7 | 72.3 | 91.9 |
| 2 | CH$_3$CH$_2$CH$_2$— | Cu | 2 | 50 | 2.3 | 78.7 | 70.8 | 90 |
| 3 | CH$_3$CH$_2$CH$_2$— | Mg | 2 | RT | 2.3 | 77 | 75.6 | 98.2 |
| 3 | CH$_3$CH$_2$CH$_2$— | Mg | 2 | 50 | 2.3 | 77 | 67.4 | 87.5 |
| 4 | CH$_3$CH$_2$CH$_2$— | H | 1 | 50 | 1.3 | 87–93 | 45–74 | **61.3 |
| 5 | CH$_3$CH$_2$CH$_2$— | Na | 1 | 50 | 0.5 | 38.8 | 19.2 | <50 |
| 6 | CH$_3$CH$_2$CH$_2$— | K | 1 | 50 | 0.5 | 25.7 | 9.8 | 38.1 |
| 7 | CH$_3$CH$_2$CH$_2$— | Ca | 2 | RT | 2.3 | 25.4 | 20.0 | 78.7 |
| 7 | CH$_3$CH$_2$CH$_2$— | Ca | 2 | 50 | 2.3 | 25.4 | 4.3 | 16.9 |
| 8 | CH$_3$CH$_2$CH$_2$— | Ba | 2 | RT | 2.3 | 41.4 | 34.6 | 83.6 |
| 8 | CH$_3$CH$_2$CH$_2$— | Ba | 2 | 50 | 2.3 | 41.4 | 3.5 | 8.5 |
| 9 | CH$_3$CH$_2$CH$_2$— | Fe | 2 | RT | 2.3 | 29.9 | 14.6 | 48.8 |
| 9 | CH$_3$CH$_2$CH$_2$— | Fe | 2 | 50 | 2.3 | 29.9 | <1 | <3.5 |
| 10 | CH$_3$CH$_2$CH$_2$— | Zn | 2 | RT | 2.3 | 29.2 | 10.9 | 37.3 |
| 10 | CH$_3$CH$_2$CH$_2$— | Zn | 2 | 50 | 2.3 | 29.2 | <1 | <3.5 |

*RT = Room Temperature about 20-25° C.
**Average of three tests

As can be seen from the above table, in the rigorous 50° C. tests, the lithium, copper and magnesium salts of the present invention, had an active material retention, or stability, of at least 81.4% after 2.3 months. In contrast to this, after only 0.5 months, the sodium and potassium salts had a stability of only 50%. The stability of the sodium and potassium salts were even poorer than the stability of the free acid. The free acid had a stability after 1.3 months at 50° C. of 61.3% based on the average of three tests (individually the results for the three test were 73.9%, 51.6% and 58.4%). After storage at 50° C. for 2.3 months the calcium salt had a stability of only 16.9%; the barium salt has a stability of only 8.5%; and there were no observable amounts of the ferrous and zinc salts (recorded in the table as <1% and calculated as <3.5% retention). Two quaternary ammonia salts (i.e., tetrabutyl ammonia and benzyltrimethyl ammonia) were also tested at 50° C. for 2.3 months and also gave poor results, i.e., 35.7% stability in the case of the tetrabutyl ammonia salt and 28.1% in the case of the benzyltrimethyl ammonia salt.

Obviously, many modifications and variations of the invention described hereinabove and below can be made without departing from the essence and scope thereof.

What is claimed is:

1. A compound having the formula:

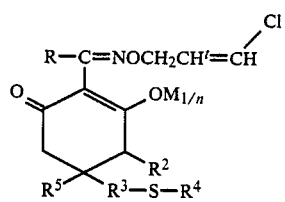

wherein M is a cation selected from the group of cupric, lithium and magnesium and n is its valence;

R is lower alkyl having 1 through 6 carbon atoms;

$R^2$ is hydrogen or alkoxycarbonyl having 2 through 6 carbon atoms;

$R^3$ is lower alkylene having 1 through 6 carbon atoms;

$R^4$ is lower alkyl having 1 through 6 carbon atoms; phenyl, or substituted phenyl having 1 through 3 substituents independently selected from the group of lower alkyl, lower alkoxyl, halo and haloalkyl having 1 through 4 carbon atoms and 1 through 3 of the same or different carbon atoms;

$R^5$ is hydrogen or lower alkyl; and the designation $=$ indicates that the compound is trans geometrically oriented with respect to the double bond.

2. The compound of claim 1 wherein said compound is a (D) optical isomer.

3. The compound of claim 1 wherein said compound is an (L) optical isomer.

4. The compound of claim 1 wherein M is cupric.

5. The compound of claim 1 wherein M is lithium.

6. The compound of claim 1 wherein M is magnesium.

7. The compound of claim 1 wherein $R^4$ is lower alkyl.

8. The compound of claim 1 wherein $R^5$ is hydrogen.

9. The compound of claim 8 wherein R is methyl, ethyl or propyl.

10. The compound of claim 9 wherein $R^5$ is hydrogen.

11. The compound of claim 10 wherein $R^2$ is hydrogen or methoxycarbonyl.

12. The compound of claim 11 wherein $R^2$ is hydrogen.

13. The compound of claim 12 wherein the group $-R^3-S-R^4$ is $-CH_2CH(CH_3)-S-CH_2CH_3$ or $-CH_2CH(CH_3)-S-CH_3$.

14. The compound of claim 13 wherein R is propyl.

15. The compound of claim 13 wherein R is ethyl.

16. The compound of claim 14 wherein M is cupric.

17. The compound of claim 14 wherein M is lithium.

18. The compound of claim 14 wherein M is magnesium.

19. The compound of claim 15 wherein M is cupric.

20. The compound of claim 15 wherein M is lithium.

21. The compound of claim 15 wherein M is magnesium.

22. A herbicidal composition comprising a herbicidally effective amount of a compound according to claim 1, or mixtures of such compounds, and a compatible carrier.

23. A herbicidal composition comprising a herbicidally effective amount of a compound according to claim 14, or mixtures thereof, and a compatible carrier.

24. A herbicidal composition comprising a herbicidally effective amount of a compound according to claim 15, or mixtures of such compounds, and a compatible carrier.

25. A method for preventing or destroying grassy plants which comprises applying a herbicidally effective amount of a compound according to claim 1, or mixtures thereof, to the foliage or potential growth medium of said plants.

26. A plant growth regulating composition which comprises an amount of a compound according to claim 1, or mixtures thereof, effective to alter the growth pattern of plants.

27. A method for regulating the growth of plants which comprises applying to the foliage of said plants or their growth medium an amount of a compound according to claim 1, or mixtures thereof, effective to alter the growth pattern of such plants.

* * * * *